United States Patent [19]

Lawson et al.

[11] Patent Number: 5,610,228

[45] Date of Patent: Mar. 11, 1997

[54] ANIONIC POLYMERIZATION INITIATORS CONTAINING ADDUCTS OF CYCLIC SECONDARY AMINES AND CONJUGATED DIENES, AND PRODUCTS THEREFROM

[75] Inventors: David F. Lawson, Uniontown; Thomas A. Antkowiak, Wadsworth; James E. Hall, Mogadore; Mark L. Stayer, Jr., Suffield, all of Ohio

[73] Assignee: Bridgestone Corporation, Tokyo, Japan

[21] Appl. No.: 471,276

[22] Filed: Jun. 6, 1995

Related U.S. Application Data

[62] Division of Ser. No. 175,294, Dec. 29, 1993, Pat. No. 5,491,230.

[51] Int. Cl.$^6$ .................................................. C08K 5/01
[52] U.S. Cl. ................... 524/573; 524/574; 524/575; 526/180; 526/337; 526/338; 526/339; 526/340
[58] Field of Search .................................. 526/180, 337, 526/338, 339, 340; 524/573, 574, 575

[56] References Cited

U.S. PATENT DOCUMENTS

| | | | |
|---|---|---|---|
| 2,849,432 | 8/1958 | Kibler et al. | 260/94.2 |
| 3,109,871 | 11/1963 | Zalinski et al. | 260/85.1 |
| 3,177,190 | 4/1965 | Hsieh | 260/94.2 |
| 3,178,398 | 4/1965 | Strobel et al. | 260/85.1 |
| 3,240,772 | 3/1966 | Natta et al. | 260/88.7 |
| 3,290,277 | 12/1966 | Anderson et al. | 260/88.2 |
| 3,317,918 | 5/1967 | Foster | 260/83.7 |
| 3,326,881 | 6/1967 | Uraneck et al. | 260/94.6 |
| 3,331,821 | 7/1967 | Strobel | 260/83.7 |
| 3,393,182 | 7/1968 | Trepka | 260/79.5 |
| 3,426,006 | 2/1969 | Nützel et al. | 260/83.5 |
| 3,439,049 | 4/1969 | Trepka | 260/624 |
| 3,652,456 | 3/1972 | Naylor | 252/431 |
| 3,856,877 | 12/1974 | Otsuki et al. | 260/677 R |
| 3,935,177 | 1/1976 | Muller et al. | 260/84.7 |
| 4,015,061 | 3/1977 | Schulz et al. | 526/178 |
| 4,026,865 | 5/1977 | Uraneck et al. | 260/42.32 |
| 4,085,265 | 4/1978 | Otsuki et al. | 526/49 |
| 4,247,418 | 1/1981 | Halasa et al. | 252/431 N |
| 4,316,001 | 2/1982 | Boileau et al. | 528/14 |
| 4,383,085 | 5/1983 | Fujimaki et al. | |
| 4,414,372 | 11/1983 | Farnham et al. | 526/190 |
| 4,429,091 | 1/1984 | Hall | 526/181 |
| 4,476,240 | 10/1984 | Hall et al. | 502/155 |
| 4,478,953 | 10/1984 | Yuki et al. | 502/155 |
| 4,515,922 | 5/1985 | Sakakibara et al. | 525/99 |
| 4,614,771 | 9/1986 | Watanabe et al. | 525/351 |
| 4,616,069 | 10/1986 | Watanabe et al. | 525/370 |
| 4,647,634 | 3/1987 | Jalics | 526/174 |
| 4,677,153 | 6/1987 | Kitahara et al. | 524/552 |
| 4,734,461 | 3/1988 | Roggero et al. | 525/293 |
| 4,735,994 | 4/1988 | Rogger et al. | 525/279 |
| 4,736,003 | 4/1988 | Schneider et al. | 526/190 |
| 4,791,174 | 12/1988 | Bronstert et al. | 525/274 |
| 4,816,520 | 3/1989 | Bronstert | 525/285 |
| 4,835,209 | 5/1989 | Kitagawa et al. | 524/507 |
| 4,843,120 | 6/1989 | Halasa et al. | 525/53 |
| 4,894,409 | 1/1990 | Shimada et al. | 524/492 |
| 4,914,147 | 4/1990 | Mouri et al. | 524/495 |
| 4,931,376 | 6/1990 | Ikematsu et al. | 526/164 |
| 4,935,471 | 6/1990 | Halasa et al. | 525/359.1 |
| 4,978,754 | 12/1990 | Ibi et al. | 544/176 |
| 5,066,729 | 11/1991 | Stayer, Jr. et al. | 525/315 |
| 5,112,929 | 5/1992 | Hall | 526/181 |
| 5,115,035 | 5/1992 | Shiraki et al. | 525/314 |
| 5,149,457 | 9/1992 | Smith | 252/182.12 |
| 5,153,159 | 10/1992 | Antkowiak et al. | 502/155 |
| 5,238,893 | 8/1993 | Hergenrother et al. | 502/155 |
| 5,248,737 | 9/1993 | Sivak et al. | 525/384 |
| 5,292,790 | 3/1994 | Shimizu et al. | 524/496 |
| 5,332,810 | 7/1994 | Kitamura et al. | 540/450 |
| 5,393,721 | 2/1995 | Kitamura et al. | 502/154 |

FOREIGN PATENT DOCUMENTS

| | | |
|---|---|---|
| 0067111A2 | 5/1982 | European Pat. Off. . |
| 0180141A1 | 10/1985 | European Pat. Off. . |
| 0207565A1 | 6/1986 | European Pat. Off. . |
| 0264506A1 | 10/1986 | European Pat. Off. . |
| 0282437A2 | 3/1988 | European Pat. Off. . |
| 0290883A1 | 4/1988 | European Pat. Off. . |
| 0316255A2 | 10/1988 | European Pat. Off. . |
| 0451603A2 | 3/1991 | European Pat. Off. . |
| 2250774 | 11/1974 | France . |
| 138070 | 10/1979 | Germany . |
| 247455 | 3/1986 | Germany . |
| 54-65788 | 5/1979 | Japan . |
| 59-164308 | 9/1984 | Japan . |
| 2117778 | 3/1983 | United Kingdom . |

OTHER PUBLICATIONS

"3–Dimethylaminopropyl–Lithium—An Analytical and Kinetic Investigation of a New Initiator System for Polymer Synthesis" by Eisenbach et al., *European Patent Journal*, vol. 11, pp. 699–704 (1975).

"A Bifunctional Anionic Initiator Soluble in Non–polar Solvents" by Beinert et al., *Makromol. Chem* 179, pp. 551–555 (1978).

(List continued on next page.)

*Primary Examiner*—Bernard Lipman
*Attorney, Agent, or Firm*—Daniel N. Hall

[57] ABSTRACT

An anionic polymerization initiator includes a carbon-lithio salt of the adduct of a cyclic secondary amine with a conjugated diene. A method of preparing an anionic polymerization initiator includes reacting an excess of a cyclic secondary amine with a conjugated diene to form an adduct; and, reacting the adduct with an organolithium compound. A method of preparing a polymer includes forming a solution of one or more anionically polymerizable monomers in a hydrocarbon solvent; and, polymerizing the monomer with an anionic polymerization initiator comprising a carbon-lithio salt of the adduct of a cyclic secondary amine with a conjugated diene. A functionalized polymer includes the termination product of a living polymer having the general formula AYLi, wherein A is a functional group derived from an anionic polymerization initiator; and, Y is a divalent polymer radical; wherein the anionic polymerization initiator is a carbon-lithio salt of the adduct of a cyclic secondary amine with a conjugated diene.

2 Claims, No Drawings

OTHER PUBLICATIONS

"An improved synthesis of p–dimethylaminophenyl–lithium" by Hallas et al., *Chemistry and Industry*, p. 620 (1969).

"Anionic Polymerization. VII Polymerization and Copolymerization with Lithium Nitrogen–Bonded Initiator" by Cheng, *American Chemical Society*, pp. 513–528 (1981).

"Anionic Polymerization Initiators Containing Protected Functional Groups and Functionally Terminated Diene Polymers" by Schulz et al., *Journal of Polymer Science: Polymer Chemistry Edition*, vol. 12, pp. 153–166 (1974).

"Anionic Polymerization Initiated by Diethylamide in Organic Solvents. I. The Use of Lithium Diethylamide as a Polymerization Catalyst and the Effect of Solvent Type on the Polymerization of Isoprene and Styrene" by Angood et al., *Journal of Polymer Science: Polymer Chemisty Edition*, vol. 11, pp. 2777–2791 (1973).

"Anionic Polymerization Intiators Containing Protected Functional Groups. II." by Schulz et al., *Journal of Polymer Science: Polymer Chemistry Edition*, vol. 15, pp. 2401–2410 (1977).

"Bifunctional anionic intiators: A critical study and overview" by Bandermann et al., *Makromol. Chem* 186, pp. 2017–2024 (1985).

"Butadiene–Styrene Copolymerization Initiated by n–BuLi/THF/t–AmOK", by Lehong et al., *Journal of Applied Polymer Science*, vol. 44, pp. 1499–1505 (1992).

"6001 Chemical Abstracts", vol. 91, p. 59 (1979).

"Copolymerization of Butadiene and Styrene by Initiation with Alkyllithium and Alkai Metal tert–Butoxides" by Wofford et al., *Journal of Polymer Science: Part A–1*, vol. 7, pp. 461–469 (1969).

"Lithium Amide Catalyzed Amine–Olefin Addition Reactions" by Schlott et al., *J. Org. Chem.*, vol. 37, No. 26, pp. 4243–4245 (1972).

"New perfectly difunctional organolithium initiators for block copolymer synthesis: Synthesis of dilithium initiators in the absence of polar additives", by Guyot et al., *Polymer*, vol. 22 (1981).

"Polymerization of Unsaturated Compounds in the Presence of Lithium Diethylamide" by Vinogradov et al., *Polymer Science U.S.S.R.*, vol. 4, pp. 1568–1572 (1963).

"Ortho Lithiation via a Carbonyl Synthon" by Harris et al., *J. Org. Chem.*, vol. 44, No. 12, pp. 2004 & 2006 (1979).

"Preparation and Reactions of Trialkyltinlithium" by Tamborski et al., pp. 237–239, Jan. 1963.

"Preparation of Some Trialkyltin–lithium Compounds" by Gilman et al., *J. Am. Chem. Soc.* 75, pp. 2507–2509 (1953).

"Some Reactions of Tributyl–and Triphenyl–stannyl Derivatives of Alkali Metals" by Blake et al., *J. Chem. Soc.*, pp. 618–622, (1961).

"Specific Functionalization of Polymers by Carboxyl Groups" by Broze et al., *Makromol. Chem.* 179, pp. 1383–1386 (1978).

"Stereospecific Addition Reaction Between Butadiene and Amines" by Imai et al., *Tetrahedron Letters* No. 38, pp. 3317–3520 (1971).

"Studies of the Anionic Polymerization of Phenyl Vinyl Sulfoxide and Its Copolymer with Styrene" by Kanga et al. *Macromolecules* 23, pp. 4235–4240 (1990).

"Synthesis of New Monomers by Addition Reactions of Diethylamine to 1,4–Divinylbenzene Catalyzed by Lithium Diethylamide" by Tsuruta et al., *Makromol. Chem.* 177, pp. 3255–3263 (1976).

"The Microstructure of Butadiene and Styrene Copolymers Sythesized with n–BuLi/THF/t–AmOK" by Lehong et al., *Journal of Applied Polymer Science*, vol. 44, pp. 1507–1511 (1992).

"Thermal Elimination of Poly(phenyl vinyl sulfoxide) and Its Polystyrene Block Copolymers" by Kanga et al., *Macromolecules* 23, pp. 4241–4246 (1990).

"Metalations of Benzyldimethylamine and Related Amines with n–Butyllithium in Ether. Deuteration to Form Ring and Side–chain Derivatives" by Jones et al., *J. Org. Chem.* 23, 663 (Mar. 1963) pp. 663–665.

"B–Lithioeamines, New Reagents for Synthesis", by L. Duhamel, J–M Poirer, *J. Am. Chem. Soc.*, 99:25, 8356–7 (1977).

ANIONIC POLYMERIZATION INITIATORS CONTAINING ADDUCTS OF CYCLIC SECONDARY AMINES AND CONJUGATED DIENES, AND PRODUCTS THEREFROM

This application is a division of application Ser. No. 08/175,294, filed Dec. 29, 1993 now U.S. Pat. No. 5,491,230.

TECHNICAL FIELD

The subject invention relates to anionic polymerization resulting in diene polymer and copolymer elastomers. More particularly, the present invention relates to polymerization employing an initiator which is the C-lithio salt of the diene adducts of cyclic secondary amines. The resulting polymers are chain-end modified and exhibit reduced hysteresis characteristics.

BACKGROUND OF THE INVENTION

In the art it is desirable to produce elastomeric compounds exhibiting reduced hysteresis. Such elastomers, when compounded to form articles such as tires, power belts and the like, will show an increase in rebound, a decrease in rolling resistance and will have less heat build-up when mechanical stresses are applied.

Previous attempts at preparing reduced hysteresis products have included high temperature mixing of the filler-rubber mixtures in the presence of selectively-reactive promoters to promote compounding material reinforcement; surface oxidation of the compounding materials; chemical modifications to the terminal end of polymers using tetramethyldiaminobenzophenone (Michler's ketone), tin coupling agents and the like and surface grafting thereon.

It has also been recognized that carbon black, employed as a reinforcing filler in rubber compounds, should be well dispersed throughout the rubber in order to improve various physical properties. One example of the recognition is provided in published European Pat. Appln. EP 0 316 255 A2 which discloses a process for end capping polydienes by reacting a metal terminated polydiene with a capping agent such as a halogenated nitrile, a heterocyclic aromatic nitrogen containing compound or an alkyl benzoate. Additionally, the application discloses that both ends of the polydiene chains can be capped with polar groups by utilizing functionalized initiators, such as lithium amides.

Organolithium polymerization initiators are also known in the art. U.S. Pat. No. 3,439,049 discloses an organolithium initiator prepared from a halophenol in a hydrocarbon medium.

U.S. Pat. No. 4,015,061 is directed toward amino-functional initiators which polymerize diene monomers to form mono- or di-primary aryl amine-terminated diene polymers upon acid hydrolysis.

U.S. Pat. No. 4,935,471 discloses dicapped polymers obtained using certain N-Li initiators, including piperidinyl and pyrrolidinyl oligoalkylamino lithiums. It has been found that piperidine-based initiators result in polymers having inferior interaction with compounding materials such as carbon black, and hence, result in little if any reduction in the hysteresis characteristics of the polymers. It has further been found that pyrrolidine-based polymers have a strong and offensive odor, making their use commercially undesirable.

The present invention provides novel initiators for anionic polymerization which become incorporated into the polymer chain providing a functional group which greatly improves the dispersability of carbon black throughout the elastomeric composition during compounding. As will be described hereinbelow, these initiators are a product of the reaction between the diene adducts of cyclic Secondary amines and an organolithium compound.

SUMMARY OF INVENTION

It is therefore, an object of the present invention to provide an anionic polymerization initiator.

It is another object of the present invention to provide an initiator as above, which when employed to polymerize an anionically polymerizable monomer, will result in a polymer having reduced hysteresis characteristics.

It is yet another object of the present invention to provide products prepared using the anionic polymerization initiators as above.

It is still another object to provide a method for the preparation of an anionic polymerization initiator as above, and polymer products therefrom.

At least one or more of the foregoing objects, together with the advantages thereof over the known art relating to anionic polymerization initiators, which shall become apparent from the specification which follows, are accomplished by the invention as hereinafter described and claimed.

In general the present invention provides an anionic polymerization initiator which comprises a carbon-lithio salt of the adduct of a cyclic secondary amine with a conjugated diene.

There is also provided according to the invention, a method of preparing an anionic polymerization initiator which comprises reacting an excess of a cyclic secondary amine with a conjugated diene to form an adduct; and, reacting the adduct with an organolithium compound.

A method of preparing a polymer comprises forming a solution of one or more anionically polymerizable monomers in a hydrocarbon solvent; and, polymerizing the monomer with an anionic polymerization initiator comprising a carbon-lithio salt of the adduct of a cyclic secondary amine with a conjugated diene.

A functionalized polymer comprises the termination product of a living polymer having the general formula AYLi, wherein A is a functional group derived from an aminoalkenyl anionic polymerization initiator; and, Y is a divalent polymer radical; wherein the artionic polymerization initiator is a carbon-lithio salt of the adduct of a cyclic secondary amine with a conjugated diene.

PREFERRED EMBODIMENT FOR CARRYING OUT THE INVENTION

As will become apparent from the description which follows, the present invention provides novel initiators for artionic polymerization of diene homopolymer and copolymer elastomers. Polymers prepared with these initiators contain a functional terminal group and it has been discovered herein that vulcanizable elastomeric compounds and articles thereof based upon such functionally terminated polymers exhibit useful properties, particularly reduced hysteresis. Hysteresis is generally known as the failure of a properly that has been changed by an external agent to return to its original value when the cause of the change is removed. When compounded to make products such as tires, power belts and the like, the polymeric products according to the invention, exhibit increased rebound, decreased rolling resistance and less heat build-up during periods of applied mechanical stress.

The present invention provides an anionic polymerization initiator which is a carbon-lithio salt of the adduct of a cyclic secondary amine with a conjugated diene, such as a 1,3-diene, and products resulting from polymerization utilizing such an initiator. Generally, the initiator is prepared by first forming the adduct of a cyclic secondary amine with the conjugated diene and then reacting the adduct with an organolithium compound preferably in the presence of a donor solvent. The resulting initiator is used to prepare any anionically-polymerized elastomer, e.g., polybutadiene, polyisoprene, polystyrene and the like, and copolymers thereof with monovinyl aromatics such as styrene, alpha methyl styrene and the like, or trienes such as myrcene. Thus, the elastomers include diene homopolymers and copolymers thereof with monovinyl aromatic polymers. Suitable monomers for polymerization employing the initiators according to the present invention include conjugated dienes having from about 4 to about 12 carbon atoms and monovinyl aromatic monomers having 8 to 18 carbon atoms and trienes, and mixtures thereof. Examples of such conjugated diene monomers and the like useful in the present invention include 1,3-butadiene, isoprene, 1,3-pentadiene, 2,3-dimethyl-1,3-butadiene and 1,3-hexadiene, and aromatic vinyl monomers include styrene, α-methylstyrene, p-methylstyrene, vinyltoluene and vinylnaphthalene. The conjugated diene monomer and aromatic vinyl monomer are normally used at the weight ratios of 95–50:5–50, preferably 85–55:15–45. It is most preferred that the polymer have a high styrene content, that is, a styrene content of about 20 percent by weight or more. The resulting polymers may also be further end-capped with a suitable reagent, as will be more fully discussed hereinbelow.

By "adduct" as used herein, it is meant the product or mixture of products arising from the addition of a secondary amine of the invention with an equimolar amount of a conjugated diene of the invention, such that the nitrogen of the secondary amine becomes bonded to a carbon of the conjugated diene. Although products of 1,4- or 4,1- addition predominate, resulting in cis- and/or trans-1-amino-2-alkenes, products of 1,2-, 2,1- and/or 3,4-addition may also be present in the mixture.

By "donor solvent" as used herein, it is meant a solvent having in its structure a heteroatom with one or more pairs of nonbonded electrons. These types of solvents can coordinate with electron-deficient species such as lithium, by "donating" their nonbonded paris of electrons, thus solvating the lithium species and reducing their state of aggregation. Such solvents include various ethers and tertiary amine compounds, such as tetrahydrofuran, glycol ethers, triethylamine, N,N,N',N'-tetramethylethylenediamine, and the like.

According to the present invention, novel compositions are produced in which the products are prepared by polymerization from the lithium salts of the diene adducts of secondary amines. This will result in a functional group or unit derived from the initiator being incorporated at the head of the polymer chain that will have unshared electron pairs. That is, it is a Lewis base. The unshared electrons can bind to Lewis acids elsewhere in the system, such as for example, to carbon black in the composition. These polymers may be useful as reduced hysteresis materials when so compounded. The initiators according to the invention include lithium compounds which are the C-metalation products of tertiary amines. That is, they are the product of replacement of C—H by C—Li. For purposes of describing this invention, such C—Li compounds are called carbon-lithio salts. More specifically, the amines are hydrocarbon amines, and the lithium salts are amine-containing organolithium compounds.

The secondary amines useful in the preparation of the adducts according to the invention, include cyclic secondary amines having from about 6 to about 16 methylene groups. Preferred cyclic secondary amines are hexamethyleneimine, heptamethyleneimine and dodecamethyleneimine. These amines substituted with a substituent group are also within the scope of the invention. Such a substituent group may include for example, dialkylaminos, dialkylaminoalkyls, alkyls, alkenyls, cycloalkyls, cycloalkenyls, bicycloalkyls, bicycloalkenyls and aralkyls, and non-interfering O-, S- and N-containing analogues thereof, where alkyl is as described below.

Other useful amines include azetidine; pyrrolidine; piperidine; morpholine; and, N-alkyl piperazines.

Examples of conjugated dieties useful in the practice of the present invention include 1,3-dienes having from about 4 to about 20 carbon atoms. Two preferred dienes are 1,3-butadiene and isoprene. Others include piperylene, myrcene, 1,3-hexadiene, 1,3-cyclohexadiene, 1,3-cycloheptadiene, 1,3-cyclooctadiene, 2,4-hexadiene, 1,3-decadiene, and various alkylbutadienes where alkyl is as described below.

The adduct intermediate thus prepared is then reacted with an organolithium compound, RLi, where R is selected from alkyls, cycloalkyls, alkenyls, aryls and aralkyls having from 1 to about 20 carbon atoms and short chain length low molecular weight polymers from diolefin and vinyl aryl monomers having up to about 25 units. Typical alkyls include n-butyl, s-butyl, methyl, ethyl, isopropyl and the like. The cycloalkyls include cyclohexyl, menthyl and the like. The alkenyls include allyl, vinyl and the like. The aryl and aralkyl groups include phenyl, benzyl, oligo(styryl) and the like. Exemplary short chain length polymers include the oligo(butadienyls), oligo(isoprenyls), oligo(styryls) and the like. Alkyllithiums are preferred.

The preferred initiators according to the invention are the reaction products of an organolithium compound with the conjugated diene and the amine adduct, as such reactants are discussed hereinabove, wherein the lithio carbon is also bonded to two hydrogen atoms to form a primary carbon-lithio salt, —CH$_2$—Li. Three preferred initiators according to the present invention include (i) the C-lithio salt of the adduct of hexamethyleneimine and 1,3-butadiene, which is represented by the formula

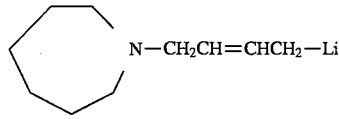

(ii) the C-lithio salt of the adduct of hexamethyleneimine and isoprene, represented by the formulae

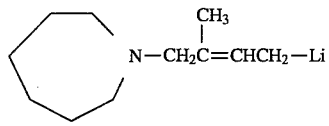

and,

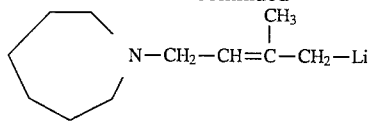

and, (iii) the C-lithio salt of the adduct of dodecamethyleneimine and butadiene, represented by the formula

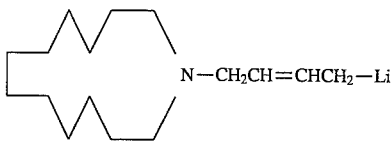

It will be appreciated that the lithium atom in each of the formulae provided herein may be at a different location in the molecule and still be within the scope of the invention.

To prepare the adduct of the invention, an equal or excess amount of the cyclic secondary amine is added to the diene, such as from about 1 to about 10 moles of amine per mole of the diene, as will be exemplified hereinbelow. The reaction is preferably catalyzed by the addition of an alkyllithium to the amine before the introduction of the diene. After a suitable reaction period, such as from about 1 to about 16 hours, the adduct is isolated by conventional techniques, such as by removing the excess amine by distillation, and then further purifying the adduct by distillation, recrystallization or the like. The adduct preferably predominantly includes one mole of amine per one mole of diene, although other proportions are also within the scope of the invention.

The C-lithio salts of these adducts may be prepared under a variety of conditions using various hydrocarbon solvents. Preferably, the solvents are those useful in anionic polymerizations, and/or polar solvents as may be desirable for improved solubility of the lithio salt or the adduct, provided that the solvents are compatible with anionic polymerizations and the subsequent polymer recovery and drying procedures. Examples of useful solvents include hexane and cyclohexane.

In one preferred embodiment of the present invention, the initiator is the lithium salt of N-(1-but-2-enyl)hexamethyleneimine, generated by the reaction of a mixture of one equivalent of N-(1-but-2-enyl)hexamethyleneimine with about one equivalent of n-butyllithium, in hexanes, cyclohexane or mixtures thereof, in the presence of about 0.5 to about 1 equivalent of the donor solvent N,N,N',N'-tetramethylethylenediamine (TMEDA), at from about −80° C. to about 100° C., for from about 1 minute to several days. Preferred reaction conditions include a reaction time of from about 30 minutes to about 24 hours, at a temperature of about 20° C. to about 50° C.

Other useful donor solvents include, for example, tetrahydrofuran (THF); ethers such as 1,2-dimethoxyethane, oligomeric oxolanyl propanes, crown ethers and the like; and, tertiary mines such as triethylamine, TMEDA, N-methylpyrrolidine, 1,1,4,7,7-pentamethyldiethylenetriamine, 1,2-dipiperidinoethane, and the like.

The initiators according to the present invention may optionally be treated with from about 1 to about 500 equivalents of a monomer before the main polymerization or co-polymerization, is made. However, this step is not an absolute limitation of the invention.

As stated above, the resulting initiators may be employed to polymerize any anionically polymerizable monomer, such as butadiene, isoprene, styrene, myrcene or the like. Suitable polymerization modifiers may also be employed, such as ethers or amines, to provide the desired microstructure and randomization of the comonomer units. The molecular weight of the polymer produced is preferably such that a proton-quenched sample will exhibit a gum-Mooney (ML/ 4/100) of from about 1 to about 150. Lower molecular weight compounds can also be made employing the invention initiators, and which are within the scope of the invention. Such lower molecular weight polymers may have a molecular weight of from several hundred to tens of thousands of mass units. These polymers can be used as viscosity modifiers and as dispersants for particulates, such as carbon black in oil.

The living polymers prepared using the initiators of the invention, have a functional amine group derived from the initiator compound and bonded at the initiation site. Thus, it is believed that substantially every resulting living polymer chain has the following general formula AYLi where A is the aminoalkenyl functional group derived from the initiator, and Y is a divalent polymer radical. A functionalized polymer according to the invention therefore, is the termination product of a living polymer having the general formula AYLi as described.

As briefly stated hereinabove, the living polymer can be terminated by treatment with a proton source, such as water, or alcohol, or tin tetrachloride, or other hysteresis-reducing terminating compounds which may contain other heteroatoms such as oxygen, nitrogen, sulfur, phosphorus, tin, non-interfering halogen, and the like. Examples of suitable terminators include carbon dioxide; isomeric vinylpyridines; dialkylaminobenzaldehydes; (bis)dialkylaminobenzophenone (Michler's ketones); dimethylimidazolidinone; Schiff bases and the like.

The living polymer may also be coupled by use of conventional coupling reagents, such as silicon tetrachloride or the like, to prepare symmetrically "dicapped" polymers. End-linked polymers prepared according to the invention, through reaction with $SnCl_4$, $C_4H_9SnCl_3$, or the like, to obtain products with greater than about 10 percent end-linking through tin, are especially desirable as elastomeric compositions having reduced hysteresis characteristics.

The polymer may be recovered from the solvent by conventional techniques. These include steam or alcohol coagulation, thermal desolventization, or any other suitable method. Additionally, solvent may be removed from the resulting polymer by drum drying, extruder drying, vacuum drying or the like. Desolventization by drum-drying, coagulation in alcohol, steam or hot water desolventization, extruder drying, vacuum drying, spray drying, and combinations thereof are preferred. An antioxidant and/or an antiozonant compound is usually added to the polymer or polymer cement at or before this stage.

The polymers of the present invention can be used alone or in combination with other elastomers to prepare an elastomer product such as a tire treadstock, sidewall stock or other tire component stock compound. In a tire of the invention, at least one such component is produced from a vulcanizable elastomeric or rubber composition. For example, the polymers according to the invention can be blended with any conventionally employed treadstock rubber which includes natural rubber, synthetic rubber and blends thereof. Such rubbers are well known to those skilled in the art and include synthetic polyisoprene rubber, styrene/ butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the polymers of the present invention are blended with conventional rubbers, the amounts can vary widely such as between about 0–80 percent by weight of the conventional rubber with from about 100–20 percent by weight of the invention polymer.

The polymers can be compounded with carbon black in amounts ranging from about 5 to about 100 parts by weight, per 100 parts of rubber (phr), with about 5 to about 80 parts being preferred and from about 40 to about 70 phr being more preferred. The carbon blacks may include any of the commonly available, commercially-produced carbon blacks but those having a surface area (EMSA) of at least 20 $m^2/g$ and more preferably at least 35 $m^2/g$ up to 200 $m^2/g$ or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following TABLE I.

TABLE I

CARBON BLACKS

| ASTM Designation (D-1765-82a) | Surface Area ($m^2/g$) (D-3765) |
|---|---|
| N-110 | 126 |
| N-220 | 111 |
| N-339 | 95 |
| N-330 | 83 |
| N-550 | 42 |
| N-660 | 35 |

The carbon blacks utilized in the preparation of the rubber compounds of the invention may be in pelletized form or an unpelletized flocculated mass. Preferably, for more uniform mixing, unpelletized carbon black is preferred. The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology*, 3rd ed., Wiley Interscience, New York 1982, Vol. 20, pp. 365–468, particularly "Vulcanization Agents and Auxiliary Materials" pp. 390–402. Vulcanizing agents may be used alone or in combination.

Vulcanizable elastomeric or rubber compositions of the invention can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

General Experimental

In order to demonstrate the preparation and properties of the initiator mixtures and elastomers according to the present invention, a number of such initiators, elastomers and compounds thereof were prepared. The initiators were then used to polymerize styrene/butadiene mixtures, with and without end-linking, as will be demonstrated hereinbelow. The polymers thus prepared were then compounded and tested for hysteresis, as was a control polymer which was conventionally prepared using an n-butyllithium initiator with tin coupling. The following is a key to terms used in the Examples and Tables:

g=grams
ml=milliliters
mequiv=milliequivalent
Pzn=polymerization
i-PrOH=isopropyl alcohol
DBPC=2,6-di-tert-butyl-para-cesol
$T_g$=the glass transition temperature

EXAMPLE 1

Preparation of the adduct of hexamethyleneimine and 1,3-butadiene

A mixture of hexamethyleneimine (49.6 g, 0.5 mol), cyclohexane (280 g), and n-butyllithium (15 ml of 1.7M solution in hexanes) was allowed to stir in a sealed container for 4 hrs. at 20°–25° C. This mixture was then agitated with 18.3 g (0.34 mol) of 1,3-butadiene, as an approximately 23% solution in hexanes (78.2 g of solution), overnight at 50° C. The contents of the bottle were treated with 10 ml of ethanol and then concentrated by distillation at ambient pressure. The product was collected in the last two cuts upon vacuum distillation at 1 Torr: a) 110°–130° C., 20.8 g, and b) 120°–140° C., 30.8 g. Both cuts had the same IR spectrum, which displayed peaks characteristic of cis and trans-butenyl substituents at 965 and 670 $cm^1$.

EXAMPLE 2

Preparation of the C-lithio salt of N-(1-but-2-enyl)hexamethyleneimine

A mixture of N-(1-but-2-enyl)hexamethyleneimine, (12.2 milliequivalent (mequiv), 1.87 g, 2 ml), n-butyllithium (12.2 mequiv, 7.2 ml of a 1.7M solution in hexanes), and N,N,N',N'-tetramethylethylenediamine ("TMEDA") (6.1 mmol, 12.2 mequiv, 3.12 ml of a 1.94M solution in hexanes) was stirred overnight at room temperature in a sealed bottle. The resulting dark orange solution contained no unreacted n-butyllithium. It was estimated to have a Li concentration of 0.99M, and was used directly to initiate polymerizations.

EXAMPLE 3

Polymerization of styrene/butadiene mixtures using the C-lithio salt of N-(1-but-2-enyl)hexamethyleneimine Polymerizations were run using the initiator generated by lithiation in the presence of TMEDA of the butadiene adduct of hexamethyleneimine. Table II lists the ingredients and conditions used in the polymerizations.

A 0.99M solution of the above initiator was added to dried, sealed, nitrogen-purged bottle, through a Viton rubber cap liner, to an 80%/20% by weight blend of butadiene and styrene in hexanes, at a level of 0.85 mequiv. Li/100 g monomer, and an additional amount of TMEDA was added at the TMEDA/Li indicated in TABLE II.

TABLE II

Polymerization of Styrene/Butadiene Mixtures

| Run No. | Amt (g) of Monomer | ml of Additional 1.94M TMEDA (TMEDA/Li) | Initiator, mequiv | Initiator, ml | Pzn temp, °C. | Pzn time, min |
|---|---|---|---|---|---|---|
| A | 66.54 | 0 (0.5) | 0.56 | 0.57 | 50 | 90 |
| B | 67.74 | 0 (0.5) | 0.57 | 0.58 | 50 | 90 |
| C | 66.50 | 0.17 (1.0) | 0.56 | 0.57 | 80 | 45 |
| D | 67.62 | 0.17 (1.0) | 0.57 | 0.58 | 80 | 45 |

The mixtures were agitated at 50° C. or 80° C. for 0.5 to 2.5 hrs., proceeding to approximately 94–98% conversion to polymer. In practice, there is considerable leeway in the reaction times and temperatures, much the same as there is leeway in the reaction vessels, type of agitation, etc., used. The treated cements then were quenched by injection with 1.5 ml or i-PrOH, treated with an antioxidant (3 ml of a mixture containing 1.6 wt % DBPC in hexane), coagulated in i-PrOH, air-dried at room temperature, then drum-dried. Suitable characterizations were performed. Analyses of the product polymers are given in Table III.

TABLE III

Analyses of Polymerization Products

| SAMPLE: | A | B | C | D |
|---|---|---|---|---|
| Polymer recovered, % | 94.5 | 94.6 | 97.8 | 95.7 |
| $T_g$, °C. (DSC, onset) | −32.5 | −37.5 | −39.8 | −41.3 |
| ML/4/100, raw | 31.9 | 99.0 | 34.8 | 100.7 |
| GPC (THF): | | | | |
| $M_n$ | 112100 | 199260 | 113560 | 144520 |
| $M_w/M_n$ | 1.26 | 2.03 | 1.46 | 2.18 |
| Comments | — | 73% coupled | — | 25% coupled |
| $^1$H NMR (CDCl$_3$), wt %: | | | | |
| Styrene | 21.1 | 21.2 | 21.2 | 21.6 |
| Block Styrene | 0.7 | 1.4 | 1.3 | 1.7 |
| 1,2- | 43.5 | 40.7 | 37.8 | 37.2 |
| 1,4- | 35.4 | 38.2 | 40.9 | 41.2 |

EXAMPLE 4

Polymerization of butadiene and styrene with the C-lithio salt of N-(1-but-2-enyl)hexamethyleneimine and end-linking with SnCl$_4$ The above procedure was followed exactly, except that after 1.5 hours of polymerization at 50° C., the polymerization mixture was treated with 0.8 equivalent of SnCl$_4$ per equivalent of Li charged. The product was worked up in the same manner as above. These showed 73% coupling in the 50° C. polymerization, and 25% coupling at 80° C., which were both run after a metalation period of approximately 24 hrs. Analyses of these polymers are also given in Table III.

EXAMPLE 5

Compounded evaluations of polymers made from the C-lithio salt of N-(1-but-2-enyl)hexamethyleneimine.

The product polymers were compounded and tested as indicated in the test recipe shown in Table V, and cured 20 minutes at 165° C. The results of the compounded evaluations are summarized in Table IV. These products exhibited improved hysteresis and enhanced interaction with carbon black, compared to unmodified elastomers. To evaluate hysteresis loss properties, the dynamic loss factor at 50° C. (tan δ) was measured by means of a viscoelastometer. In general, the smaller the tan δ value, the lower the hysteresis loss.

TABLE IV

Analyses of Compounded Products

| Polym. No. | Polymer | ML/4 — Raw | ML/4 — Cpd | Bound Rubber, % | #1 Dispersion Index, % | Dynastat, 1 Hz, tan δ 50° C. |
|---|---|---|---|---|---|---|
| | Sn-Coupled$^a$ Control (BuLi initiator) | 74 | 84 | 36.4 | 91.7 | 0.090 |
| B | HMI—Bd$^b$—Li/SnCl$_4$, 50° C. | 99 | 122 | 55.7 | 71.4 | 0.087 |
| C | HMI—Bd—Li, 80° C. | 35 | 66 | 33.7 | 96.3 | 0.086 |
| D | HMI—Bd—Li/SnCl$_4$, 80° C. | 101 | 105 | 48.0 | 70.7 | 0.099 |

$^a$)Sample A was not tested because its $T_g$ was significantly higher than the others.
$^b$)HMI is hexamethyleneimine; Bd is 1,3-butadiene

TABLE V

Low-Oil Test Formulation for Evaluation of Hysteresis

| Ingredient | Mix Order | Parts per Hundred Parts of Rubber | |
|---|---|---|---|
| Polymer | 1 | 100 | Masterbatch: |
| Naphthenic oil | 2 | 10 | 145–155° C., |
| Carbon black, N-351 | 3 | 55 | 60 RPM (drop after 5 min, @ 155–175° C.) |
| ZnO | 4 | 3 | |
| Antioxidant | 5 | 1 | |
| Wax blend | 6 | 2 | |
| Total Masterbatch: | | 171 | |
| Stearic acid | | 2 | Final: |
| Sulfur | | 1.5 | 77–95° C., |
| Accelerator | | 1 | 40 RPM |
| Total Final: | | 175.5 | |

Hence, the products according to the present invention have been shown to have similar or improved hysteresis characteristics, as compared with the control polymer compound.

Thus, it should be evident that the initiators and products of the present invention are highly effective in providing elastomers and products having reduced hysteresis characteristics.

Based upon the foregoing disclosure, it should now be apparent that the use of the initiators and products described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, the adducts, reactants, monomers, terminators, solvents, methods or the like according to the present invention are not necessarily limited to those discussed above. Thus, the scope of the invention shall include all modifications and variations that may fall within the scope of the attached claims.

What is claimed is:

1. A vulcanizable elastomer formed by compounding a polymer with from about 5 to about 80 parts by weight of carbon black, per 100 parts by weight of said polymer;

wherein said polymer is prepared by polymerizing a solution of one or more anionically polymerizable monomers in a hydrocarbon solvent with an anionic polymerization initiator;

wherein said anionic polymerization initiator comprises a carbon lithio salt of the adduct of a cyclic secondary amine with a conjugated diene.

2. A treadstock compound formed from the vulcanizable elastomer of claim 1.

* * * * *